United States Patent [19]
Mason

[11] Patent Number: 5,931,785
[45] Date of Patent: *Aug. 3, 1999

[54] ULTRASONIC TRANSDUCER HAVING ELEMENTS ARRANGED IN SECTIONS OF DIFFERING EFFECTIVE PITCH

[75] Inventor: Martin K. Mason, Andover, Mass.

[73] Assignee: Hewlett-Packard Company, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/961,485

[22] Filed: Oct. 30, 1997

[51] Int. Cl.⁶ ........................................ A61B 8/00
[52] U.S. Cl. ................................................ 600/459
[58] Field of Search ...................... 600/459, 437, 600/440, 443, 447; 367/138

[56] References Cited

U.S. PATENT DOCUMENTS

| | | | |
|---|---|---|---|
| 2,837,728 | 6/1958 | Schuck | 340/9 |
| 5,115,810 | 5/1992 | Watanabe et al. | 600/459 |
| 5,291,090 | 3/1994 | Dias | 310/334 |
| 5,488,956 | 2/1996 | Battelt et al. | 600/459 |
| 5,546,946 | 8/1996 | Souquet | 600/459 |
| 5,575,290 | 11/1996 | Teo et al. | 600/456 |
| 5,608,690 | 3/1997 | Hossack et al. | 367/138 |
| 5,651,365 | 7/1997 | Hanafy et al. | 600/459 |
| 5,653,235 | 8/1997 | Teo | 600/447 |
| 5,840,032 | 11/1998 | Hatfield et al. | 600/443 |

*Primary Examiner*—William E. Kamm
*Assistant Examiner*—Ali M. Imam
*Attorney, Agent, or Firm*—Mark Z. Dudley

[57] ABSTRACT

An ultrasonic imaging system may include a transducer array having a novel distribution of transducer elements. Preferred embodiments of the system include a transducer having a linear, curved linear, or matrixed array of piezoelectric transducer elements. The transducer may include a novel distribution of transducer elements applied to the elevation elements, wherein the elevation aperture is divided into three sections, that is, a central section having an array of fine-pitched elements, and upper and lower sections. The novel distribution of transducer elements may be applied to the elevation elements wherein the system is adapted for a first mode of operation characterized as a near-field mode (e.g., at shallow depths), such that the transducer elements in the central section are activated to effect various purposes, e.g., beam steering and electronic focusing, and the transducer elements in the outer sections are generally not activated. The system is also adapted for a second mode of operation characterized as a far-field mode, wherein the transducer elements in both the central and outer sections are activated.

7 Claims, 7 Drawing Sheets

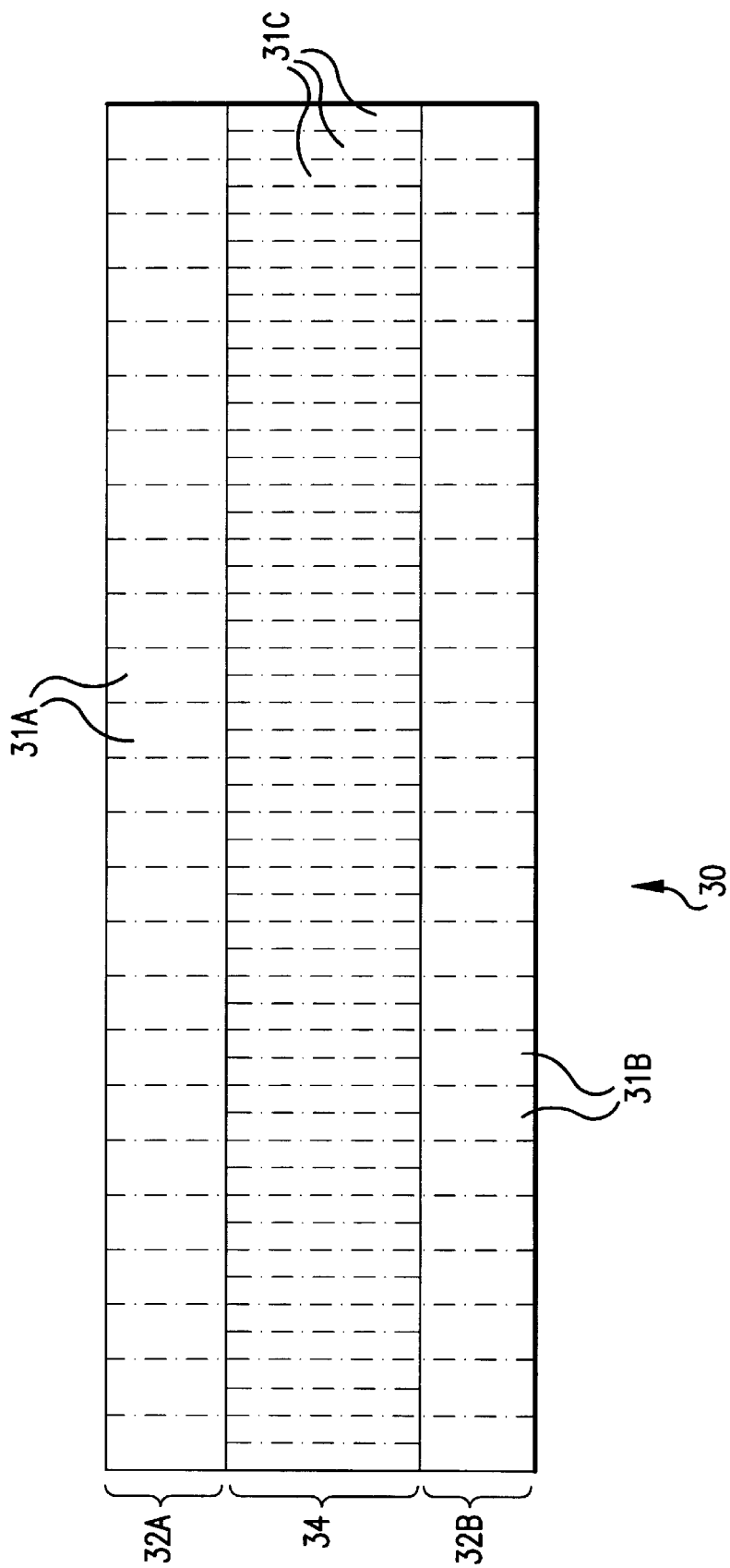

ULTRASONIC TRANSDUCER HAVING ELEMENTS ARRANGED IN SECTIONS OF DIFFERING EFFECTIVE PITCH

FIELD OF THE INVENTION

The invention generally relates to ultrasonic imaging systems and more particularly to a transducer operable in an ultrasonic imaging system.

BACKGROUND OF THE INVENTION

Ultrasonic imaging systems are known for detecting or imaging the internal structures of liquid, solid, and semi-solid materials. In operation, such apparatus typically includes an ultrasonic transducer that generates a beam of acoustic signals, which is transmitted into the material of interest and is reflected by various gradients or other physical features of the material. The beam may be focused at various depths within the material and may also be scanned so that the reflected acoustic signals may be used to provide image data about various aspects of the material.

In a particular application of ultrasonic systems in the field of medicine, ultrasonic imaging systems are used to examine or monitor the anatomical features of a patient. For example, the reflected signals may be received, analyzed, and processed to produce an image display that is representative of blood flow, tissue, or the structure of internal organs, such as the heart.

In a phased array ultrasound imaging system, an ultrasound transducer includes an array of transducer elements. The system includes a multiple channel transmitter and a multiple channel receiver connected through a transmit/receive switch to the transducer. Each transmitter channel causes a selected transducer array element to transmit an ultrasound pulse into an object being imaged. The transmitted ultrasound energy is steered along a transmit scan line and is focused by applying appropriate delays to the pulses transmitted from each transducer array element, so that the transmitted energy adds constructively at a desired focal point to form a transmit beam. A part of the transmitted ultrasound energy is reflected back to the transducer array by various structures that are in the path of the transmitted ultrasound energy.

The reflected ultrasound energy from an object or structure arrives at the array elements at different times. The received signals are amplified and are delayed in separate receiver channels and then are summed in a receive beam former to form a receive beam. The delay for each channel is selected such that the receive beam is steered at a desired angle and is focused at a desired depth. The delays may be varied so as to focus the beam at progressively increasing depths along a receive scan line as the ultrasound energy is received.

Ultrasound energy is transmitted along multiple transmit scan lines in a desired scan pattern, such as a sector scan, and the received signals are processed to produce an image of the region of interest.

In order to obtain the highest quality image, both the transmit beam and the receive beam could be focused at each point in the area being imaged. However, the time required to obtain an image in this manner would be prohibitive. In most prior art systems, the transmit beam is typically focused at a single focal depth, and the receive beam is dynamically focused in the scan plane. For both transmit and receive beams, the elevation focus is typically established by means such as an acoustic lens mounted on the transducer. As a result, the transmit beam is out of focus at points displaced from the transmit focal point, and the receive beam is out of focus in the elevation plane, except at a fixed focal point. These factors cause those portions of the image that are displaced from the focal points to be degraded in quality.

More recently, arrays with variable-elevation focusing have been developed. A typical elevation-focused transducer in a medical ultrasound imaging system may include an array of 64 to 256 elements. Each transducer element is divided in three or more segments in the elevation plane. The segments of each transducer element can be activated via respective channels in signal processing circuitry for focusing in the scan plane and the elevation plane. A dynamic aperture may also be effected when different active apertures of the transducer are activated by selectively enabling different groups of transducer elements and segments. See, for example, U.S. Pat. No. 5,301,168, assigned to the assignee of the present application, which discloses an ultrasound transducer having rows and columns of transducer elements, and U.S. Pat. No. 5,462,057, assigned to the assignee of the present application, which discloses a phased array ultrasound transducer divided into transducer elements arranged side-by-side in the lateral direction.

However, as the array size increases, the demand for channels will increase as well. There are a limited number of beam forming channels, such as 256 or less, available in a typical ultrasound imaging system. For best use of these beam forming channels, it is known to divide each element into several elevation elements and to use symmetry to connect elements at equal distance from the center line of the transducer array. A typical array includes a distribution of transducer elements in what is known as a 1.5D linear array or a 1.5D curved linear array (CLA) transducer probe. Each transducer element is divided into one central element segment and two, four, or more smaller outer element segments. The plural segments may be arranged in an inner segment array, first outer segment array, second outer segment array, and so on. One may appreciate that each element of the array is thus divided into segments to allow electronic focusing in both the scan and elevation planes. The advantage of this approach is that the elevation focal point can be changed to allow the desired focus at a range of depths in the image. For example, if there are n channels devoted to each lateral element, then each lateral element can be divided into (n−1) elevation elements.

When operating a segmented array having an acoustic lens for elevation focusing, dynamic elevation focusing will provide only modest improvements in the far field, i.e., at points in a range beyond the focal point of the lens. However, great improvement is possible in the near field, i.e., at points in a range within the focal point of the lens, if the elevation dimension of the individual elements is small enough to prevent large phase errors across the width of the elements during focusing. Hence, segmented arrays having many small elements are attractive for use in many applications.

However, if the entire elevation aperture is filled with small elements, the demand for channels for signal processing cannot be met in a practical or cost-effective fashion. While features such as high resolution acoustic imaging, electronic beam steering, and electronic focusing provide many advantages, there remains a need for improvement in the design and construction of an ultrasonic probe suitable for effecting improved elevation focusing in the near-field.

SUMMARY OF THE INVENTION

The present invention provides an improved ultrasound imaging system suitable for use in varied applications, such as in medicine, non-destructive test and analysis, and in other fields of use.

I have found that when effecting beam focusing in the near-field in an ultrasound imaging system, a transducer having a novel distribution of elements, wherein the distribution incorporates central and outer sections of elements, and wherein the effective pitch of elements in a central section is different than the effective pitch in the outer sections, will offer improved focusing at high frequencies in a near-field mode of operation. In particular, a novel distribution of elements along the elevation plane may be provided, whereby the elevation aperture is divided into at least three sections, a central section with a plurality of elements, and upper and lower outer sections each having at least a single element. The effective pitch of the plurality of elements in the central section is less than the effective pitch of the elements in at least one of the upper and lower outer sections. (Stated in equivalent but converse terms, the effective pitch of the plurality of elements in at least one of the upper and lower outer sections is coarser than the effective pitch of the elements in the central section. Hence, the effective pitch of the elements in the central section may be considered as being "fine", or the effective pitch of the elements in one or more of the outer sections may be considered as being "coarse".)

The terms "effective pitch" are used herein to denote a pitch that is set by: a) the particular physical spacing of independently activated elements, or b) effecting certain electrical connections to a series of elements to create sets of plural, coupled elements, wherein the sets in the series are operated in lieu of the individual elements. In the latter instance, a series of elements may be divided into sets of plural elements; each of the elements in a set are coupled in a way such that the coupled elements act as one element, and the pitch of the series of elements is thus replaced by the effective pitch of the sets of elements, such that the sets of elements will typically exhibit an effective pitch that is greater than the original pitch of the series of elements.

In a particular feature of the invention, the central section is advantageously utilized when the system is operated in the near-field (i.e., inside the natural focus of the transducer), and therefore the operation of the transducer array at high frequencies is improved, while only a limited number of signal processing channels need be allocated to provide elevation plane focusing of certain ones of the transducer element segments in the central section. As a result, an ultrasound imaging system may be constructed and operated so as to better accomplish elevation plane focusing in the near-field, at high frequencies, and with use of fewer channels, as compared to imaging systems operated according to the prior art.

In a departure from the prior art, and in a particular aspect of the present invention, an ultrasonic probe system may be constructed wherein the transducer probe includes a transducer array having a novel effective pitch of transducer elements.

As used herein, the term "novel distribution" refers to a characteristic of the effective pitch of certain transducer elements, and sub-elements if present, in a face of a transducer array, wherein a finer lateral pitch of elements or sub-elements per unit area are located in a central section of the face of the transducer array, as compared to the lateral pitch of elements or sub-elements per unit area that are located in one or more of the remaining section(s) of the face. As a result, the terms "novel distribution" also refers to a characteristic of the distribution of the transducer elements, and sub-elements if present, wherein the active surfaces of most if not all of the transducer elements thus located in the central section are less than the active areas of transducer elements located in other sections.

The effective pitch of the transducer elements or sub-elements thus located in the central section may be considered as being provided in certain embodiments wherein the elements or sub-elements are physically constructed to be closely-spaced, or "finely pitched". Alternatively, the effective pitch of the transducer elements or sub-elements thus located in the central section may be considered as being provided in certain embodiments wherein the lateral pitch of the elements or sub-elements in the central and outer sections are the same or similar, but wherein certain pairs, triads, . . . etc. of elements in the outer sections are electrically connected together so as to each operate as a single element, thus effectively achieving the desired difference in the effective pitch of the elements in the outer sections with respect to the effective pitch of the elements or sub-elements in the central section.

Accordingly, the terms "novel distribution" and "effective pitch" as used herein denotes that the pitch of the transducer elements or sub-elements in the central section is finer (i.e., less) than the pitch of the transducer elements or sub-elements in the remaining section(s). Hence, for the purposes of this description, the term "outer" when describing elements or sub-elements will refer to such elements or sub-elements other than those located in the central section.

Preferred embodiments of the system include a transducer probe having a linear, curved linear, or matrixed array of piezoelectric transducer elements wherein the transducer array exhibits the novel distribution of the transducer elements.

In another aspect of the present invention, the transducer probe includes a novel distribution of transducer elements applied to the elevation elements, wherein the elevation aperture is divided into three sections, that is, a central section having an array of fine-pitched elements, and upper and lower sections each having respective elements of coarser pitch, or that are connected in such a way as to effect a coarse pitch.

In another aspect of the present invention, an ultrasonic probe system may be constructed wherein the transducer probe includes a transducer array having a novel distribution of transducer elements relative to both the elevation and scan planes. In this aspect of the present invention, an ultrasonic probe system may be constructed wherein the transducer probe includes a transducer array having a novel distribution of transducer elements relative to one or both of the elevation and scan planes, wherein the elements distributed across the face of the transducer have varying size. For example, the transducer probe may include a novel distribution of transducer elements applied to the elevation elements, wherein the elevation aperture is divided into at least three sections, that is, a central section includes an array of elements, and upper and lower outer sections each include respective elements connected in parallel, and wherein the elements forming the elevation aperture are flanked by additional left and right outer sections. The upper, lower, left, and right outer sections are distributed about, and adjacent to, the central section so as to surround the central section.

In another aspect of the invention, the novel distribution of transducer elements may be applied to the elevation elements wherein the system is adapted for a first mode of operation, that is, in a near-field mode (e.g., at shallow depths), such that the transducer elements in the central section are activated to effect improved operation at high frequencies, and the transducer elements in the outer sections are substantially inactive. The system is also adapted for a second mode of operation, that is, in a far-field mode, wherein the transducer elements in both the central and outer sections are activated.

A particularly preferred embodiment of an imaging system constructed according to the present invention includes a transducer having a physical beam-focusing means, such as an acoustic lens, and a transducer element array having plural transducer elements, such as may be formed of a relaxor ferroelectric ceramic material, wherein the transducer has a first surface, an opposing surface and a central axis. A set of electrodes is electrically coupled with the first surface of the transducer and a second set of electrodes is electrically coupled with the opposing surface of the transducer. Individual electrodes are thus electrically coupled with certain ones of the transducer elements. The system further includes electronic switches for selecting electrodes so as to activate certain portions or sections of the transducer element array. A controller dynamically configures the electronic switches to vary the arrangement of active elements while the transducer remains substantially stationary. The system further includes beam forming means for effecting beam steering and electronic focusing. The system is adapted for operation to effect beam focusing such that, when operable in a near-field mode, the beam forming channels are devoted to operation of selected transducer elements in the central section, and when operable in a far-field mode, the beam forming channels are devoted to operation of selected transducer elements in the central and outer sections.

Accordingly, an ultrasonic imaging system may be provided to include a transducer probe constructed according to the present invention that performs desirable effects such as electronic beam steering and electronic focusing, and improved operation at high frequencies, but which requires fewer beam-forming channels.

In another feature of the present invention, the contemplated system thus advantageously uses smaller apertures to provide good beam focusing at shallow focal lengths, while providing full apertures at greater focal lengths.

In another feature of the present invention, scan plane focusing and elevation plane focusing may be successfully employed in the preferred embodiments to effect high resolution acoustic imaging with use of a reduced number of beam forming channels.

BRIEF DESCRIPTION OF THE DRAWINGS

The foregoing and other features and advantages of the invention will be apparent from the following more particular description of preferred embodiments of the drawings, in which like reference characters refer to the same parts throughout the different views. The drawings are not necessarily to scale, emphasis instead being placed upon illustrating the principles of the invention.

FIGS. 2A, 2B, and 2C are plan views of preferred embodiments of a transducer element array constructed according to the present invention for inclusion in an ultrasonic probe useable in an ultrasonic imaging system.

DETAILED DESCRIPTION OF THE PREFERRED EMBODIMENT

Figure 1A:
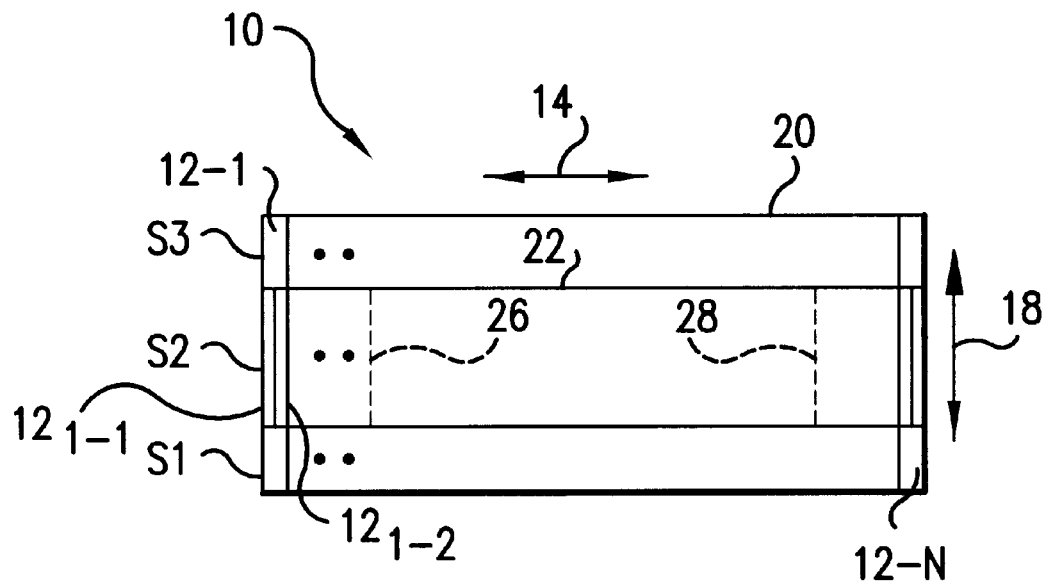
FIGS. 1A and 1B are a simplified plan view and a simplified side view, respectively, of an ultrasonic probe assembly constructed according to the present invention.
Figure 1B:
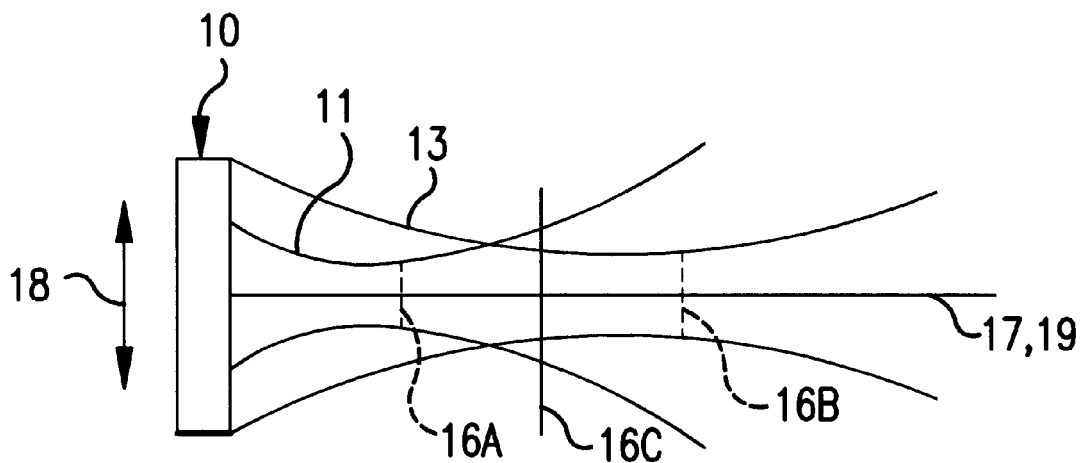

A first embodiment of an ultrasound transducer 10 suitable for implementation of the present invention is shown in FIGS. 1–2. The transducer is divided into plural transducer $12_1, 12_2, \ldots 12_N$. In the example of FIG. 1, each transducer element $12_1, 12_2, \ldots 12_N$ is divided into three segments S1, S2 and S3 in the elevation direction 18. For clarity, the segment S2 will be considered as the central segment and the two outer segments S1, S2 may also be considered as the upper and lower segments, respectively. Although not shown in FIG. 1, additional outer segments are contemplated and may be considered as the first upper segments, second upper segment, etc. In a particular feature of the invention, each transducer element $12_1, 12_2, \ldots 12_N$ in the central segment S2 is divided to include at least two sub-elements $12_{1-1}, 1_{1-2}$ arranged side-by-side in the lateral direction 14. Hence, the elements in the central segment S2 comprise a plurality of sub-elements $12_{1-1}, 12_{1-2}$ wherein the sub-elements $12_{1-1}, 12_{1-2}$ exhibit an effective pitch that is less than the effective pitch of the associated elements in the outer segments S1, S3.

A typical transducer for a medical ultrasound imaging system may include 64 to 256 elements. The segments S1 to S3 of each transducer element can be individually activated for transmission and reception of ultrasound energy. In certain embodiments of the invention, different active apertures of the transducer are activated by selectively enabling different groups of transducer elements and segments. For example, in a preferred embodiment of the invention applied to a phased array transducer, a far field aperture 20 includes substantially all elements and segments of the transducer 10, both in the lateral and elevation directions. A near field aperture 22 includes only the segment S2 of the transducer elements in the central portion of the transducer 10, and preferably only the sub-elements 12 in the elements located between dashed lines 26 and 28. The far field aperture 20 is used for transmitting and receiving ultrasound energy in the far field of a region of interest, and the near field aperture 22 is used for transmitting and receiving ultrasound energy in the near field of the region of interest.

Typical transmit beam patterns for a phased array version of the ultrasound transducer 10 are understood as follows. By appropriately delaying the pulses applied to the transducer elements in the active aperture, as known in the art, the transmitted ultrasound energy is steered in a desired direction with respect to the transducer array and is focused at a desired focal depth. A side elevation view of the transducer 10 is shown in FIG. 2. The near field aperture 22 transmits ultrasound energy having a beam pattern 30 focused in the near field at a focal depth 16A. The far field aperture 20 transmits ultrasound energy having a beam pattern 13 focused in the far field at a focal depth 16B. Each beam pattern may be steered with respect to a normal to the transducer 10. In order to form transmit beam patterns 11 and 13, each transducer element in the active aperture is energized with a pulse having a delay selected to focus the transmitted ultrasound energy at the focal depth 16A or 16B and to steer the transmitted ultrasound energy. The near field beam pattern 11 can be represented as a transmit scan line 17, and the far field beam pattern 34 can be represented as a far field transmit scan line 19. The near field and far field transmit scan lines 17 and 19 are co-linear, originate at the center of the active aperture of transducer 10 and have an angle θ in the direction 14 with respect to a normal to transducer 10. The transmitted ultrasound energy produces ultrasound echoes from various structures in the region of interest. The ultrasound echoes are received by the transducer 10 and are converted to electrical signals. The beam patterns shown in FIG. 1 are transmitted at a plurality of steering angles to form a desired scan pattern, and the received signals are processed as known to produce signals for generating an image of the region of interest.

By appropriate phasing of the received signals in a beamformer, a receive beam is formed. The receive beam may be steered at a desired steering angle and is dynamically focused at progressively increasing depths as ultrasound echoes are received, so that the receive beam remains in focus as echoes are received from progressively increasing depths. An arbitrary boundary 16C located between focal depths 16A and 16B separates the near field and the far field. That is, the near field extends from the transducer 10 to boundary 16C, and the far field extends from boundary 16C to the desired maximum imaging depth. It will be understood that the boundary 16C will vary in depth depending on the locations of the focal depths 16A and 16B.

Figure 2B:
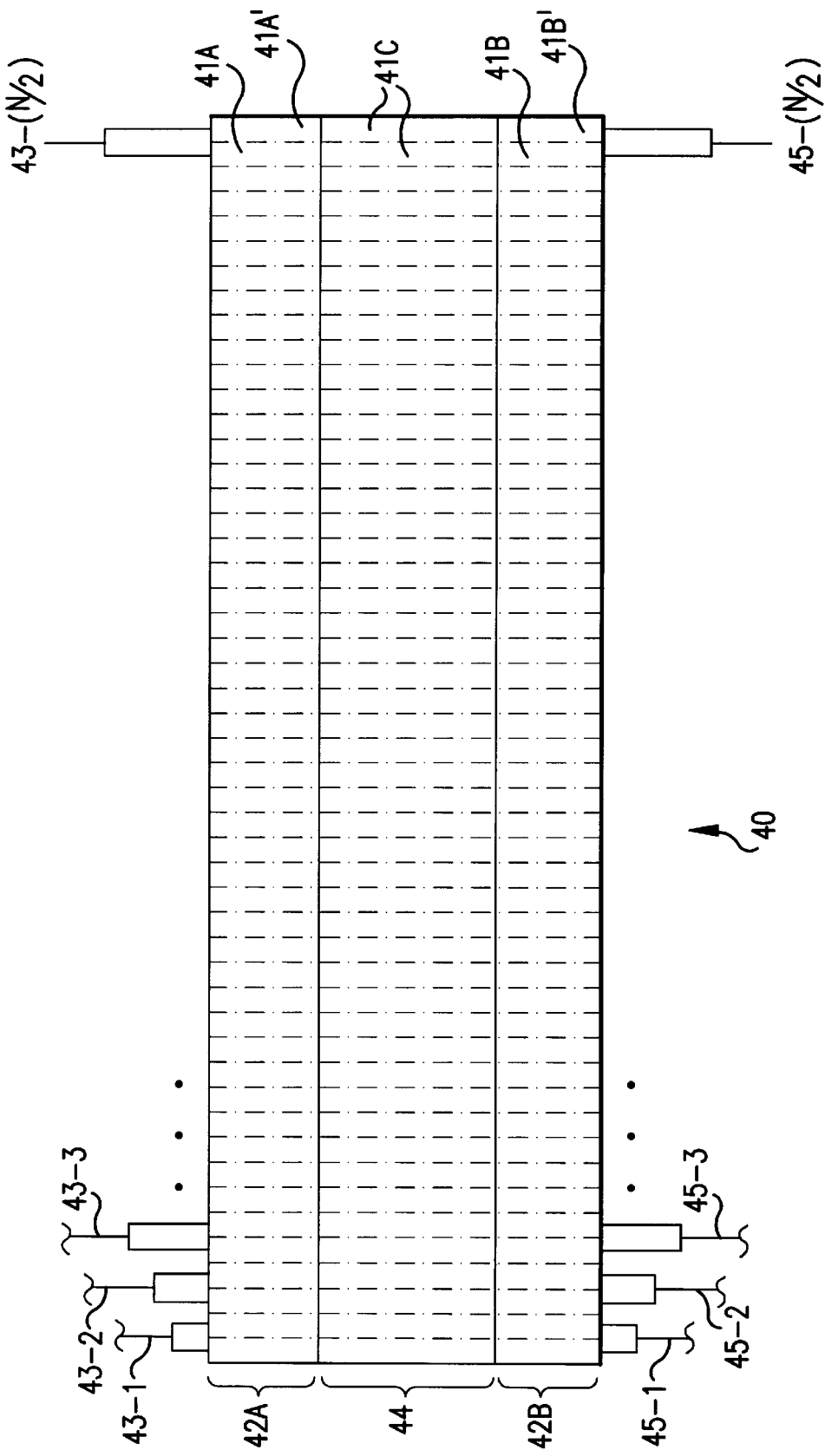
Figure 2C:
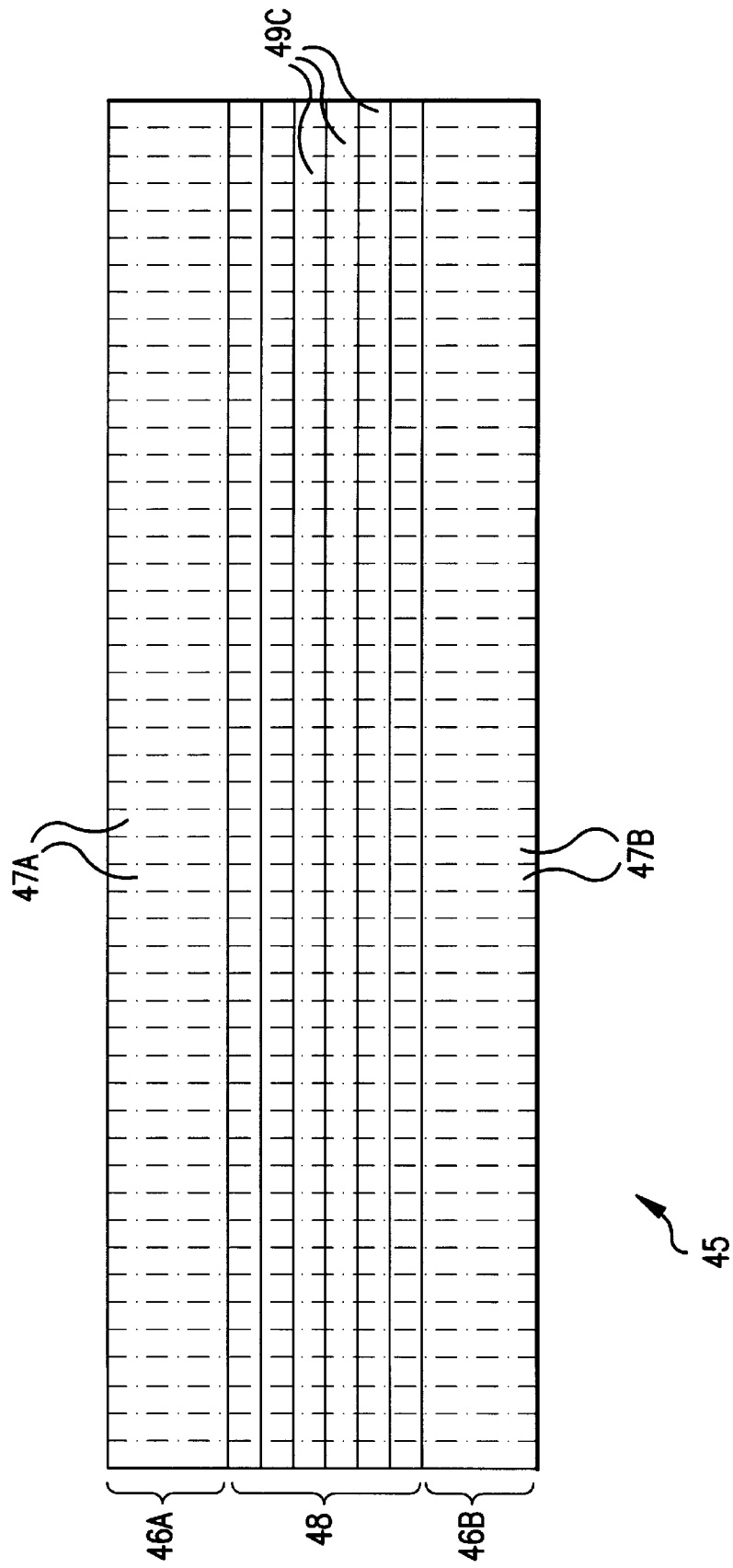

As illustrated in FIGS. 2A–2C, additional preferred embodiments include a second preferred embodiment of a transducer array 30, a third preferred embodiment of a transducer array 40, and a fourth preferred embodiment of a transducer array 45, wherein a novel distribution of plural transducer elements in arrays 30, 40, 45 may be employed to obtain the benefits of the present invention.

In FIG. 2A, in the array 30, the elevation aperture is divided into three sections: a central section 34 having an array of finely spaced transducer elements 31C, thus achieving the desired fine effective pitch, and upper and lower sections 32A, 32B each having respective plurality of transducer elements 31A, 31B.

In FIG. 2B, in the array 40, the elevation aperture is divided into three sections: a central section 44 having an array of transducer elements 41C, and upper and lower sections 42A, 42B each having respective plurality of transducer elements 41A, 41B. In the array 40, the elements in the outer sections 42A, 42B exhibit the same or similar lateral spacing as the elements in the central section 44. Hence, to achieve the desired difference in the effective pitch in the outer sections 42A, 42B with respect to the central section 44, one skilled in the art may see that selected pairs (or more) of adjacent elements are connected together such that each pair functions as a single element. For example, upper signal lines 43-1, 43-2, . . . 43-(N/2) and lower signal lines 45-1, 45-2, . . . 45-(N/2) connect to sets of paired elements 41A and 41A', or to sets of paired elements 41B and 41B', respectively. In alternative embodiments, in lieu of the connections to an element pair in a set, the connections may be made to three, four, . . . etc. elements in a set to effect the desired effective pitch.

In FIG. 2C, in the array 45, the elevation aperture is divided into three sections: a central section 48 having an array of transducer elements 49C, and upper and lower sections 46A, 46B each having respective plurality of transducer elements 47A, 47B. Arrays 40 and 45 differ in that the lateral pitch of the elements 49C in the central section 48 is less than the lateral pitch of the elements 47A, 47B in the outer sections 46A, 46B. Such difference may be accomplished, for example, by appropriate dicing of the surface of the array 45.

In FIG. 2B, for certain applications, certain ones of the element pairs 41A, 41A' in the upper section 42A are connected in parallel with certain ones of the element pairs 41B, 41B' in the lower section 42B such that the array 40 may be operated as a 1.5D linear or curved linear array. Similarly, in FIG. 2C, for certain applications, certain ones of the elements 47A in the upper section 46A are connected in parallel with certain ones of the elements 47B in the lower section 46B such that the array 40 may be operated as a 1.5D linear or curved linear array.

However, those skilled in the art will appreciate that the arrays described herein need not be limited to application as a 1.5D array configuration; for example, the arrays described herein may be configured in alternative embodiments to include a N x N matrix of elements and thus function as a full 2D array.

Figure 3A:
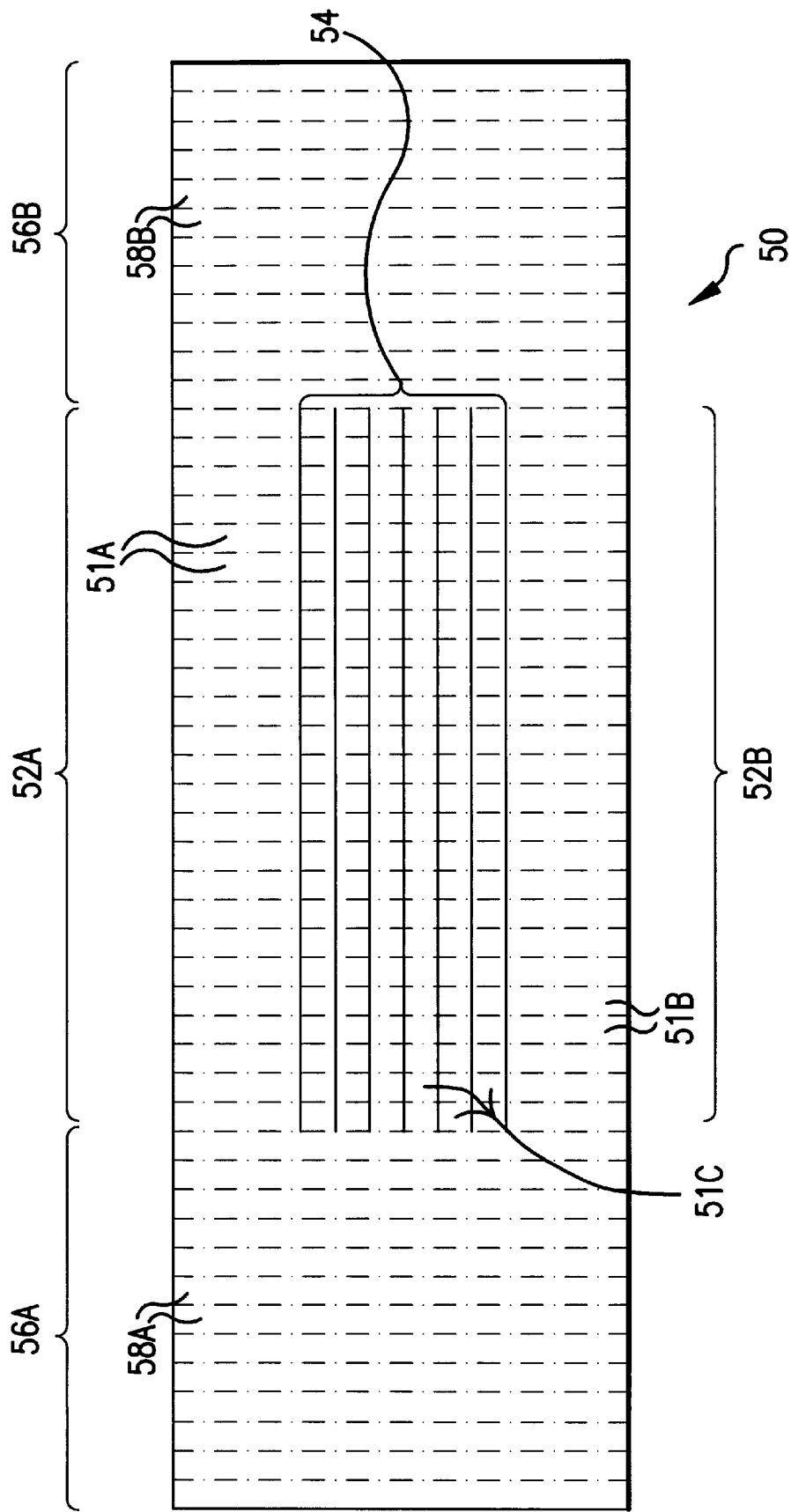
FIGS. 3A and 3B are plan views of third and fourth embodiments of a transducer element array constructed according to the present invention for inclusion in an ultrasonic probe useable in an ultrasonic imaging system.
Figure 3B:
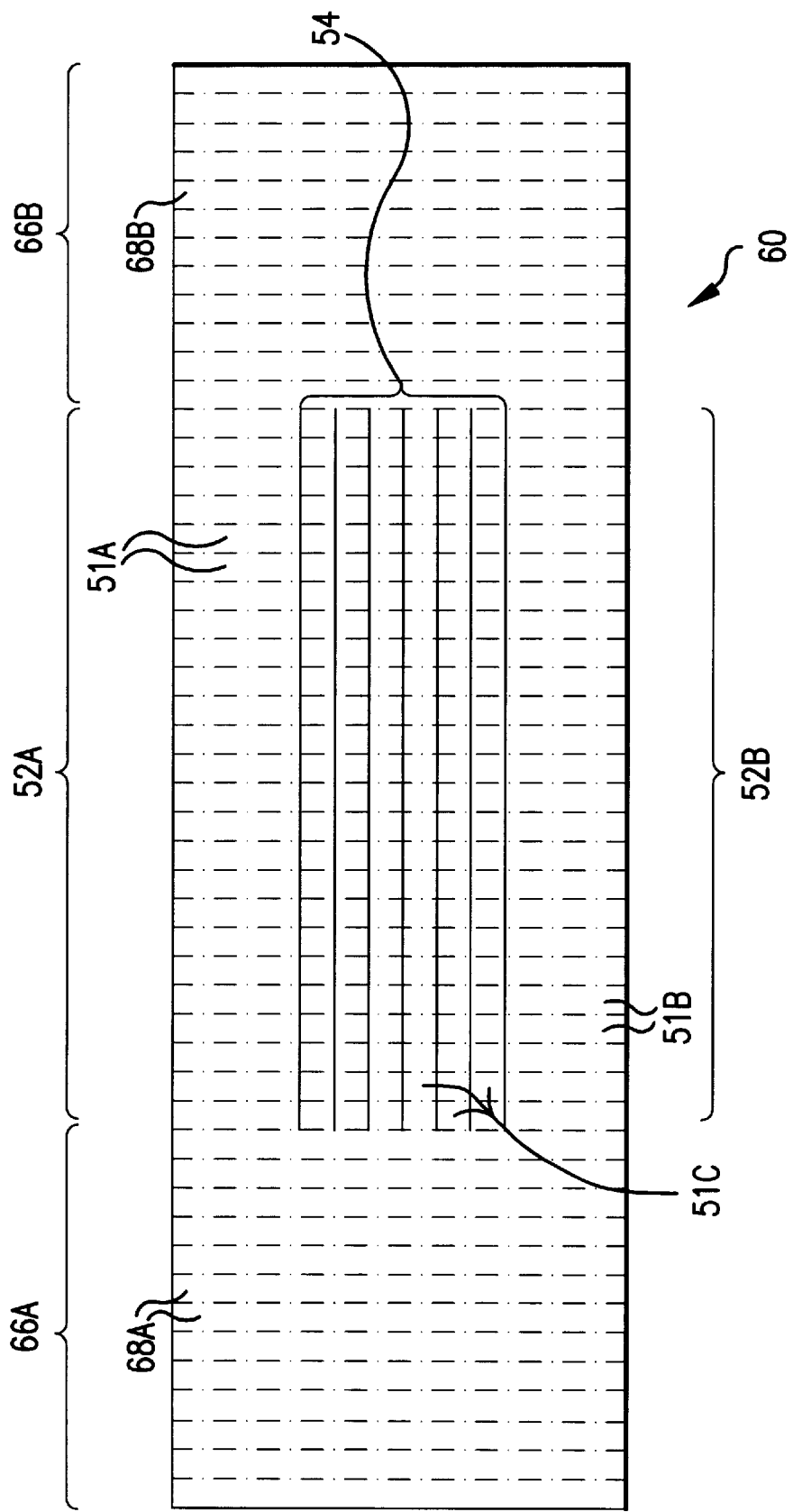

As illustrated in FIGS. 3A and 3B, third and fourth preferred embodiments of a transducer array 50, 60 are shown for operation as a phased transducer array wherein a novel distribution of plural transducer elements may be employed to obtain the benefits of the present invention. In the array 50, the elevation aperture is divided into three sections: a central section 54 having an array of elements 51C, and upper and lower outer sections 52A, 52B each having a respective plurality of transducer elements 51A, 51B; and the remainder of the active surface is arranged in left and right outer sections 56A, 56B that include additional plural transducer elements 58A, 58B respectively. In most applications, certain pairs of the elements 51A in the upper section 52A are connected in parallel with certain pairs of the elements 51B in the lower section 52B such that the array 40 may be operated as a 1.5D phased array. The left and right outer sections 56A, 56B are distally located adjacent the combination of the central section 54, upper section 52A, and lower section 52B. In array 60, the remainder of the active surface is arranged in left and right outer sections 66A, 66B that include plural transducer elements 68A, 68B, respectively,. Left and right outer sections 66A, 66B are each arranged to exhibit less lateral pitch than found in left and right outer sections 56A, 56B. Left and right outer sections 66A, 66B are distally located adjacent the combination of the central section 54, upper section 52A, and lower section 52B.

Scan plane and elevation plane focusing may be successfully employed in the illustrated embodiments to effect improved high resolution acoustic imaging with use of a reduced number of beam forming channels. For example, the array 40 may be operated in a near-field mode (e.g., at shallow depths) such that the fine-pitched transducer elements 41C in the central section 44 are activated for purposes such as beam steering and electronic focusing, while the transducer elements 41A, 41B in the outer sections 42A, 42B are not activated. When operated in a far-field mode, most if not all of the transducer elements in both the central section 44 and outer sections 42A, 42B may be activated. As a further example, the array 50 is preferably operated in a near-field mode (e.g., at shallow depths) such that the transducer elements 51C in the central section 54 are activated for purposes such as beam steering and electronic focusing, while the transducer elements 51A, 51B in the outer upper and outer lower sections 52A, 52B and the transducer elements 51A, 51B in the outer right and outer left sections 52A, 52B need not be operated. However, when operated in a far-field mode, the transducer elements in most if not all of the sections (i.e., central section 44, outer upper and outer lower sections 52A, 52B, and outer right and outer left sections 52A, 52B) are operated.

Figure 4:
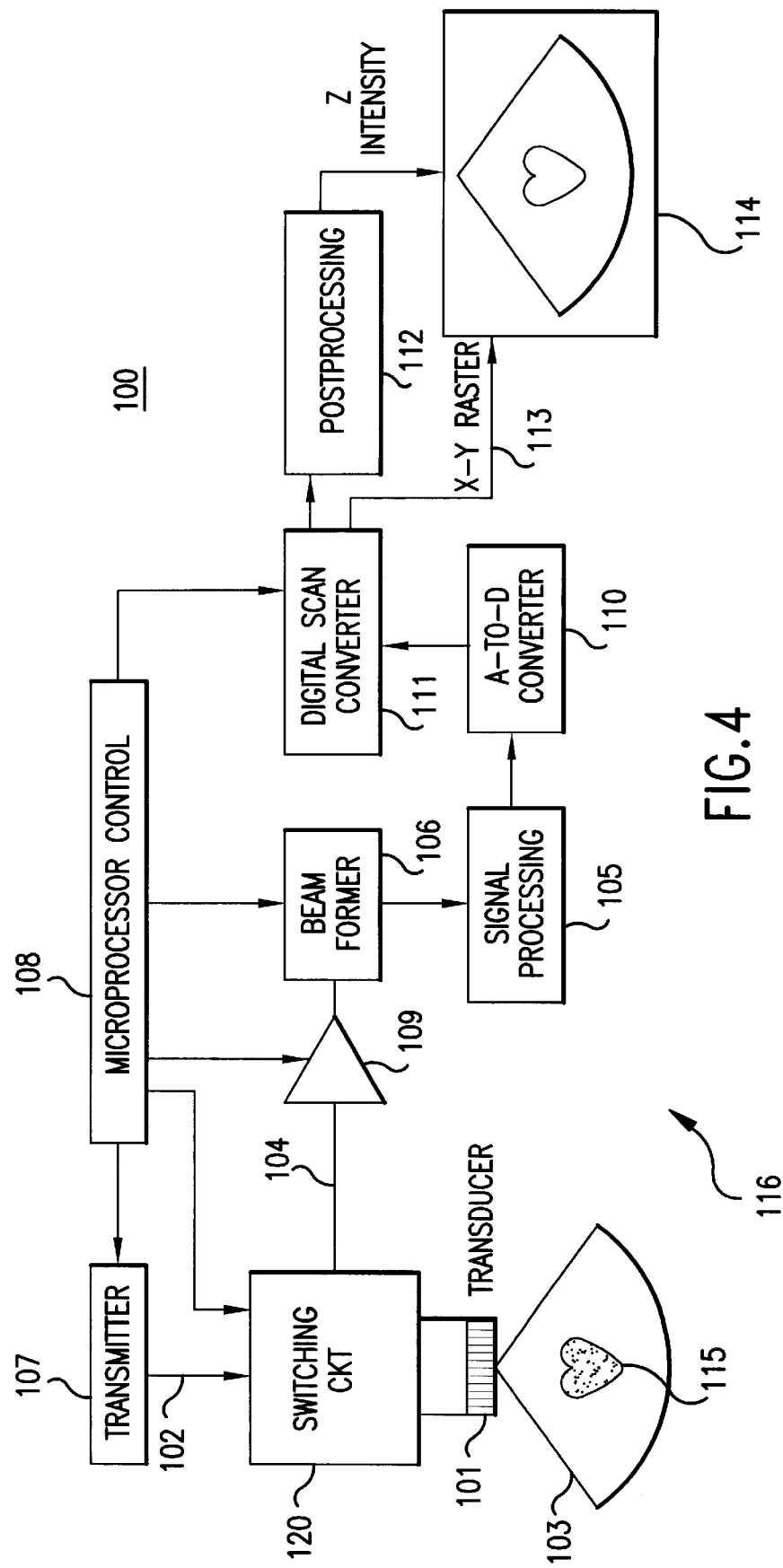
FIG. 4 is a simplified schematic view of a preferred embodiment of a novel imaging system constructed according to the present invention.

As schematically shown in FIG. 4, a preferred embodiment of an ultrasonic imaging system 100 constructed according to the present invention includes a transducer having therein a transducer array 101 constructed according to the teachings herein. Preferably, the transducer array 101 is constructed according to the teachings herein with reference to the arrays 10, 30, or 45 of FIGS. 1–3.

The transducer array 101 includes plural piezoelectric transducer elements with each transducer element preferably formed of a region of piezoelectric material, such as a relaxor ferroelectric ceramic material, separated from other such regions by non-conductive filler. Preferred piezoelectric materials, such as lead zirconate titanate (PZT) ceramic, may also be formed of "composites", in which a piezoelectric ceramic and a polymer are combined for an improved range of properties. Other transducer arrays may be made of electrostrictive materials, which are highly polarizable by the application of a DC bias voltage. Lead magnesium niobate-lead titanate (PMN-PT) is one example of an electrostrictive ceramic. The transducer array 101 has a first surface, an opposing surface, and a central axis. A first set of substantially planar electrodes (not shown) may be electrically coupled with a first surface of the transducer array 101 and a second set of substantially planar electrodes is electrically coupled with an opposing surface of the transducer array 101. The electrodes are electrically coupled with respective elements in the transducer array 101 for enabling selective activation of the elements according to operation in near-field and far-field modes, as taught herein.

As shown in FIG. 4, an ultrasound imaging system 100 includes an electrical stimulus 102, such as a pulse, provided to transducer array 101, causing the transducer array to transmit an ultrasonic acoustical wave 103. The ultrasonic wave is transmitted into a region of interest and is partially reflected by an object in the region of interest. In the illustrated embodiment, the region of interest lies within a human body and the object, is for example, a heart 115. The reflected wave ("echo") is received by the transducer array 101 which produces an electrical current 104 that is indicative of the echo. Various properties of signal 104, such as its amplitude and phase, are then analyzed by a signal processing section to determine information about the object, such as its size, location, and velocity. See for example U.S. Pat. No. 5,060,651, U.S. Pat. No. 5,301,168, and U.S. Pat. No. 5,462,057, the contents of which are incorporated herein by reference.

More specifically, FIG. 4 shows a signal processing section 116 having microprocessor 108 for controlling each of a transmitter 107, receiver 109, multichannel beam former 106, switching circuit 120, and digital scan converter 111. The echo signal 104 from transducer array 101 is sent to the preamplifier 109 and then in series to beam former 106, signal processor 105, A/D converter 110, and digital scan converter 111. The z-component of the echo signal is sent to post processor 112, and the resulting z-intensity is displayed on CRT screen 114. The x-y component is sent via x-y raster 113 and displayed on CRT screen 114. Any number of different transmitting and imaging processing techniques may be used.

In a particular feature of the illustrated system 100, the limited number of channels in the signal processing section 116 may be optimized for effecting beam focusing. For example, the limited number of channels that are not allocated for effecting scan plane focusing may be allocated by the switching circuit 120 for effecting the differing modes of near-field and far-field operation as described hereinabove. Due to the novel distribution of transducer elements, the limited number of channels thus allocated during near-field operation may then be efficiently used to effect signal processing in signal processing circuit 105 so as to allow improved focusing in the near field. As a result, the overall quality of beam focusing is improved with use of the same or fewer number of beam-forming channels that are employed for effecting beam focusing in systems operated according to the prior art.

The contemplated system 100 thus advantageously performs scan plane and elevation plane focusing at, e.g., smaller apertures to provide good overall beam focusing at short focal lengths, while nonetheless providing full apertures during operation at long focal lengths. Fixed elevation plane focusing may be provided as known in the art by, for example, a fixed acoustic lens integrated in the transducer 101.

Preferred embodiments of the system 100 may be understood to provide allocation of a channels with respect to a multiple element array by way of high voltage multiplexor chips in the switching circuit 120 to switch channels to the appropriate element segments, or to element pairs, triads, etc., as described herein.

Preferred embodiments of the system 100 are contemplated as being amenable to inclusion of additional techniques known in the art for improving beam focusing, steering, and aperture control.

For example, preferred embodiments of the system 100 may be understood to perform beam focusing that may be divided into two or more splice zones. Splicing has the additional benefit of providing multiple transmit focal points and thereby better image uniformity than that of a single splice. In performing beam splicing, two or more transmit beams are transmitted at the same steering angle, but at different focal depths. The received signals in the region of each transmit focal point are "spliced" together to form a single receive line at each steering angle. The transmitted beams are focused both in elevation plane and in scan plane by energizing different apertures of the transducer at different focal depths. Since the spliced receive line is made up of received signals from regions where the transmitted beams are relatively focused, image quality is improved. Preferred embodiments may take advantage of beam splicing techniques as disclosed, for example, in U.S. Pat. No. 5,301,168, issued to Miller and assigned to the assignee of the present application, the contents of which are incorporated herein by reference.

Also as disclosed in U.S. Pat. No. 5,462,057, issued to Hunt et al. and assigned to the assignee of the present application, the contents of which are incorporated herein by reference, preferred embodiments of system 100 may employ a phased array ultrasound imaging system wherein a high quality image is obtained by a combination of line splicing and parallel receive beam forming. In particular, the array 101 may include at least two selectable elevation apertures. The transmitter 107 includes means for transmitting ultrasound energy along the near field transmit scan line with a first elevation aperture and for transmitting ultrasound energy along the far field transmit scan line with a second elevation aperture that is larger than the first elevation aperture. The signal processing section 116 includes appropriate means in receiver 109 for receiving signals along the first and second near field receive scan lines with the first elevation aperture and for receiving signals along the first and second far field receive scan lines with the second elevation aperture. Thus, ultrasound energy transmitted along the near field and far field transmit scan lines is focused, both in the scan plane and in the elevation plane. The receiver means includes means for varying the receive angle during reception of the ultrasound echoes to compensate for spatial variations in the transmitted ultrasound energy.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An ultrasonic transducer system, comprising: a transducer having a plurality of transducer elements arranged in a transducer array wherein a first plurality of central elements are distributed in a central section and second and third pluralities of upper and lower outer elements are respectively distributed in upper and lower sections, wherein the central, upper, and lower sections extend in the array along an azimuthal direction and are separated along an elevation direction, each of said central elements in the central section being aligned along the elevation direction with at least an adjacent upper element and an adjacent lower element so as to define a respective elevation aperture wherein each central element is individually connectable apart from at least the combination of the upper and lower adjacent elements so as to be respectively subject to activation for the production of ultrasound energy therefrom, and wherein each of the central elements further comprise a plurality of individually connectable sub-elements, wherein the sub-elements exhibit an effective pitch along the azimuth of the array that is less than the respective effective pitch of either of the adjacent upper and lower elements.

2. The system of claim 1, wherein the distribution of the transducer elements according to the elevation aperture further comprises in the upper and lower sections a distribution of multiple outer elements connected in parallel.

3. The system of claim 2, and wherein the central section is flanked by additional left and right outer sections.

4. The system of claim 3, and wherein the sub-elements forming the central section have a pitch that is less than the pitch of the elements that form the left and right outer sections.

5. The system of claim 1, further comprising:
   electric switch and control means for activation of selected ones of the transducer elements, wherein the system is adapted for a first mode of operation characterized as a near-field mode, wherein substantially all of the sub-elements in the central section are activated and the transducer elements in the upper and lower sections are not activated, and wherein the system is adapted for a second mode of operation characterized as a far-field mode, wherein substantially all of the transducer elements in both the central and upper and lower sections are activated.

6. The system of claim 1, wherein the array of transducer elements is configured in an array configuration selected from the group consisting of: linear, curved linear, and matrixed element configurations.

7. An ultrasonic imaging system, comprising:
   a transducer having a plurality of transducer elements arranged in a transducer array, wherein a first plurality of central elements are distributed in a central section and second and third pluralities of upper and lower outer elements are respectively distributed in upper and lower sections, wherein the central, upper, and lower sections extend in the array along an azimuthal direction and are separated along an elevation direction, each of said central elements in the central section being aligned along the elevation direction with at least an adjacent upper element and an adjacent lower element so as to define a respective elevation aperture wherein each central element is individually connectable apart from at least the combination of the upper and lower adjacent elements so as to be respectively subject to activation for the production of ultrasound energy therefrom, and wherein each of the central elements further comprise a plurality of individually connectable sub-elements, wherein the sub-elements exhibit an effective pitch along the azimuth of the array that is less than the respective effective pitch of either of the adjacent upper and lower elements;
   a first plurality of electrodes electrically coupled with a first surface of the transducer and a second plurality of electrodes respectively coupled with an opposing surface of the transducer;
   plural electronic switches for selecting electrodes so as to activate selected elements of the transducer element array;
   a controller for dynamically configuring the electronic switches to vary the arrangement of active elements; and
   a beam former for subjecting the acoustic beam to electronic focusing;
   wherein the system is adapted for a first mode of operation characterized as a near-field mode wherein the beam former is devoted to operation of selected central elements, and wherein the system is adapted for a second mode of operation characterized as a far-field mode wherein the beam former is devoted to operation of selected central, upper, and lower transducer elements.

* * * * *